(12) United States Patent
Cai et al.

(10) Patent No.: US 11,718,625 B2
(45) Date of Patent: Aug. 8, 2023

(54) NEAR-INFRARED FLUORESCENT MOLECULE ACTIVE TARGETING FOLATE RECEPTOR AND PREPARATION METHOD THEREOF

(71) Applicant: NANJING NUOYUAN MEDICAL DEVICES CO., LTD, Jiangsu (CN)

(72) Inventors: Huiming Cai, Jiangsu (CN); Yiqing Wang, Jiangsu (CN)

(73) Assignee: NANJING UOYUAN MEDICAL DEVICES CO., LTD, Jiangsu (CN)

( * ) Notice: Subject to any disclaimer, the term of this patent is extended or adjusted under 35 U.S.C. 154(b) by 0 days.

(21) Appl. No.: 17/596,423

(22) PCT Filed: Nov. 27, 2020

(86) PCT No.: PCT/CN2020/132366
§ 371 (c)(1),
(2) Date: Dec. 9, 2021

(87) PCT Pub. No.: WO2022/082932
PCT Pub. Date: Apr. 28, 2022

(65) Prior Publication Data
US 2022/0267330 A1 Aug. 25, 2022

(30) Foreign Application Priority Data

Oct. 23, 2020 (CN) .......................... 202011145658.3

(51) Int. Cl.
*C07D 487/04* (2006.01)
*A61K 49/00* (2006.01)
*C09K 11/06* (2006.01)
*G01N 21/64* (2006.01)

(52) U.S. Cl.
CPC ........ *C07D 487/04* (2013.01); *A61K 49/0021* (2013.01); *C09K 11/06* (2013.01); *G01N 21/6458* (2013.01); *C09K 2211/1029* (2013.01); *C09K 2211/1059* (2013.01)

(58) Field of Classification Search
CPC .. A61K 49/00; A61K 49/0021; C07D 487/04; C09K 11/06; C09K 2211/1059; G01N 21/6458
USPC ................................ 424/1.11, 1.65, 9.1, 9.6
See application file for complete search history.

(56) References Cited

FOREIGN PATENT DOCUMENTS

| CN | 108449940 A | 8/2018 | |
|---|---|---|---|
| CN | 112010862 B | 3/2021 | |
| KR | 1020200012254 A | 2/2020 | |
| WO | 2019018238 A1 | 1/2019 | |
| WO | WO-2022082932 A1 * | 4/2022 | ........... C07D 487/04 |

OTHER PUBLICATIONS

Office action dated Dec. 7, 2020 for the priority, Chinese patent application No. 202011145658.3, Chinese Patent Office.
Office action dated Dec. 20, 2020 for the priority, Chinese patent application No. 202011145658.3, Chinese Patent Office.
Grant Notification for the priority dated Mar. 11, 2021, Chinese patent application No. 202011145658.3, Chinese Patent Office.
Search report dated Nov. 2, 2020 for the priority, Chinese patent application No. 202011145658.3, Chinese Patent Office.
Search report dated Feb. 20, 2021 for the priority, Chinese patent application No. 202011145658.3, Chinese Patent Office.

* cited by examiner

*Primary Examiner* — D. L. Jones
(74) *Attorney, Agent, or Firm* — ArentFox Schiff LLP

(57) ABSTRACT

The present disclosure relates to the fields of near-infrared surgical navigation fluorescent molecules, cell marker imaging and so on, and in particular discloses an active targeting near-infrared fluorescent small molecule structure and a preparation method thereof. The present disclosure prepares the active targeting near-infrared fluorescent small molecule with pemetrexed disodium and derivatives thereof as active targeting groups by utilizing an organic total synthesis method. Such active targeting near-infrared fluorescent molecule has the advantages of high active targeting property, strong specificity, good water solubility, high fluorescence quantum yield and so on.

3 Claims, 10 Drawing Sheets

NEAR-INFRARED FLUORESCENT MOLECULE ACTIVE TARGETING FOLATE RECEPTOR AND PREPARATION METHOD THEREOF

CROSS-REFERENCE TO RELATED APPLICATION

This application is a 371 U.S. national phase stage of PCT/CN2020/132366, filed Nov. 27, 2020, which claims priority to Chinese patent application No. 202011145658.3, filed Oct. 23, 2020, the contents of each of which are incorporated herein by reference in its entirety.

FIELD OF THE INVENTION

The present disclosure relates to the fields of near-infrared surgical navigation fluorescent molecules, cell marker imaging and so on, in particular to an active targeting near-infrared fluorescent small molecule and a preparation method thereof.

BACKGROUND OF THE INVENTION

Indocyanine green (ICG) is a hydrophilic fluorescent tracer, with a molecular weight about 776 Da. It has also been widely used in the assessment of liver function, assessment of cardiac output, and fundus angiography before being used for fluorescent tracing. Under the irradiation of near-infrared fluorescence with the wavelength of 780 nm, it can emit fluorescence with the wavelength of 830 nm, and has good penetrability. Fluorescence detection can be carried out on some deep tissues with ICG. After entering blood, ICG can be rapidly combined with plasma protein to form protein-coated ICG nano-molecules, which can be enriched in tumor tissues through an EPR effect and phagocytized by a reticuloendothelial phagocytosis system, so as to participate in tumor development and lymph node tracing. In addition, studies have shown that ICG will not increase the risk of short-term and long-term complications in patients, and has high biological safety. Therefore, the ICG not only can be used to realize noninvasive deep angiography and lymph radiography, but also can be used for instant intraoperative fluorescent tracing in surgical operation. However, according to the results observed in a large number of clinical and live animal experiments reported in the literature in recent years, ICG as a tumor fluorescent tracer still has the following problems:

1) Low fluorescence emission efficiency (quantum yield is less than 1% in an aqueous solution), and high requirement to equipment sensitivity. According to Drug Administration Regulations of China, a maximum injection dosage of the ICG in the human body should be less than 2 mg/kg, and at this dosage, the concentration of the ICG in the human body tumors is 10-1000 nM according to the literature report and our own detection data, while the effective detection range of most existing devices is 10-1000 μM, which are different by 1000 times.

2) It was found in clinical practice that the metabolic rates of ICG in tumor and normal tissue are not quite different, and it needs to wait at least 12 hours to generate sufficient fluorescence contrast (tumor: normal tissue), which increases the burden on the hospital and patient.

It may thus be seen that to develop a new generation of fluorescent tracer with high fluorescence quantum yield, active tumor targeting, and capability of being rapidly eliminated in normal tissues may make up for the defects of ICG in actual use, and has very high scientific research and clinical application values. Researches have shown that integrin has a higher level of expression on surfaces of a plurality of malignant tumor cells or neovascular endothelial cells of tumor tissues, for example, gastric cancer, ovarian cancer, and breast cancer, while the expression of cells of normal tissues or mature vascular endothelial cells is very little. The integrin targeting the tumor tissues to be highly expressed may achieve precise delivery of drugs. At present, pemetrexed disodium and derivatives thereof, as a mature and safe tumor-targeted drug, can be closely combined with the integrin on the cell surface to inhibit and destroy the normal metabolic process of folic acid dependence in cells and inhibit cell replication, so as to inhibit the growth of tumor. The pemetrexed disodium and derivatives thereof have better in vivo stability while ensuring good targeting property thereof, and have greater potential in modification of near-infrared fluorescent small molecules.

SUMMARY OF THE INVENTION

The present disclosure aims at providing a near-infrared fluorescent small molecule active targeting folate receptor and a preparation method of this molecule. A molecular formula of this molecule is as follows:

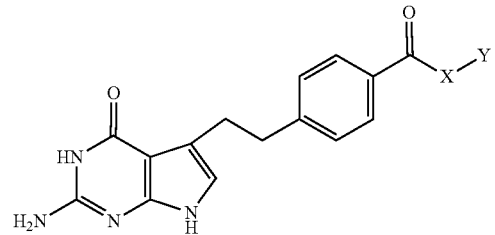

In the above, x is selected from the following structures:

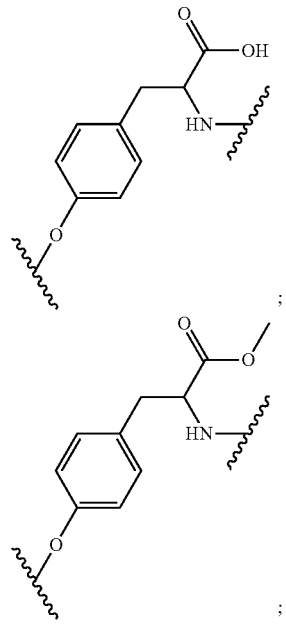

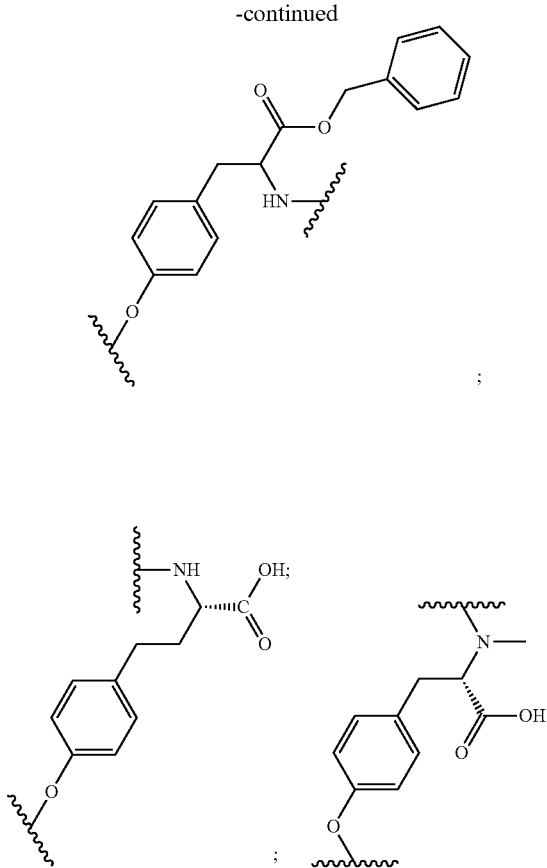

Y is selected from S0456 and derivatives thereof; and

Y is linked to X by forming an ether bond with a phenolic moiety of a tyrosine side chain of X.

Further, the near-infrared fluorescent small molecule active targeting folate receptor has a following structure:

M is independently selected from H, Na, and K.

A following molecular structure is taken as an example:

A preparation process thereof includes following steps:
S1, synthesizing S0456;
S2, synthesizing a pemetrexed targeted drug and preparing Pemetrexed-Tyr; and
S3, reacting Pemetrexed-Tyr and S0456 to generate Pemetrexed-Tyr-S0456.

Further, the above step S1 includes following steps:

S11, mixing and heating 4-hydrazinophenylsulfonic acid, 3-methyl-2-butane, and glacial acetic acid to 110-130° C., refluxing the resultant for 16-20 hours in nitrogen atmosphere, precipitating in ethyl acetate, then filtering and collecting a crude product in the form of pink solid, dissolving the obtained product in methanol, dropwise adding a dissolving solution into a solution of potassium hydroxide and isopropanol under mild condition, and filtering and washing the crude mixture to obtain a product brown solid 1, with a structural formula as follows:

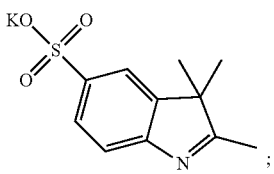

S12, adding the product 1 and 1,4-butyl sultone into a toluene solution in nitrogen atmosphere to be heated at 100-120° C. for 40-55 h, cooling mixed materials to room temperature, adding a crude mixture into methanol to be stirred for 30 minutes; followed by precipitating, filtering, and collecting, dissolving the resultant again in a mixture of water and methanol at 2:1, and slowly adding the mixed solution into acetonitrile with a dropping funnel; filtering a precipitate and collecting a pink solid product 2, with a structural formula as follows:

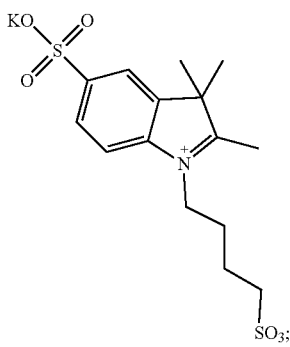

S13, refluxing and heating the product 2, (chloromethylene)dimethyliminium chloride (Vilsmeier-Haack Reagent™), and anhydrous sodium acetate in anhydrous ethanol for 6-8 hours in nitrogen atmosphere, cooling reaction mixture to room temperature, followed by filtering, washing with ethanol and methanol, performing suction filtration, drying, and collecting a green solid product 3, with a structural formula as follows:

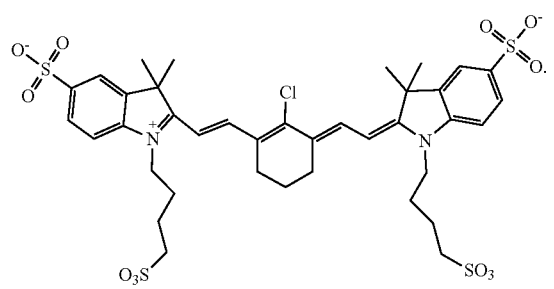

Further, in the above step S2, synthesizing a pemetrexed targeted drug includes following steps:

dissolving a pemetrexed hydrolytic acid in DMF, sequentially adding Hexafluorophosphate Azabenzotriazole Tetramethyl Uronium (HATU), O-tert-butyl-L-tyrosine tert-butyl ester hydrochloride, and DIEA into a flask, stirring until the resultant is dissolved completely, reacting at room temperature for 25-35 minutes under the protection of nitrogen, dropwise adding the reacted solution into an HCl solution to generate a light yellow precipitate, and drying the light yellow precipitate to obtain a solid product 4, with a structural formula as follows:

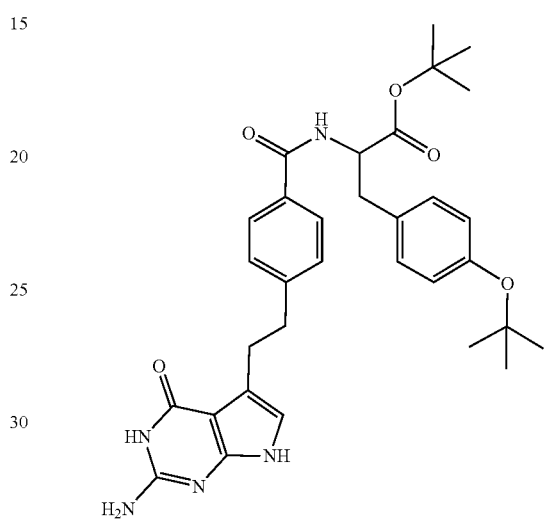

Preparing Pemetrexed-Tyr includes following steps:

putting the product 4 into a round-bottom flask, adding an aqueous TFA solution, stirring the mixture for two hours, adding the resultant into methyl tert-butyl ether, followed by precipitating and filtering, and drying in vacuum to obtain a product 5, with a structural formula as follows:

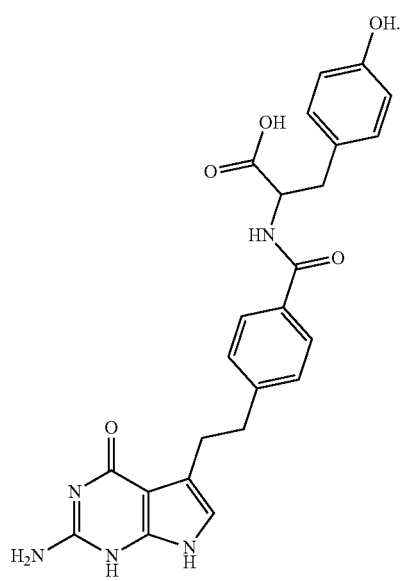 [SMILES: Nc1nc(=O)c2c(CCc3ccc(C(=O)NC(Cc4ccc(O)cc4)C(=O)O)cc3)c[nH]c2[nH]1]

Further, the above step S3 includes following steps:

S31, to an aqueous solution of S0456, dropwise adding a Pemetrexed-Tyr trianion solution with pH of 10-12 at 18-28° C.;

S32, raising the temperature of reaction mixture to 85-95° C., stirring for 40-55 minutes, and monitoring formation of 7 by TLC;

S33, after the product is formed, cooling the reaction mixture to room temperature, and transferring the reaction mixture into stirred acetone as a stable flow through a cannula to obtain a green precipitate;

S34, filtering the precipitate on a sintering funnel under the vacuum by an air pump, and washing the resultant with acetone; and S35, drying the green powder-like solid to obtain Pemetrexed-Tyr-S0456.

Compared with the prior art, the advantages of the present disclosure lie in:

the present disclosure discloses a preparation method of an active targeting near-infrared fluorescent molecule, which prepares the active targeting near-infrared fluorescent small molecule with pemetrexed disodium and derivatives thereof as active targeting groups by utilizing an organic total synthesis method. Such active targeting near-infrared fluorescent molecule has the advantages of high active targeting property, strong specificity, good water solubility, high fluorescence quantum yield and so on, and has great development potential in the fields of tumor surgical navigation imaging and medical cell marking.

DETAILED DESCRIPTION OF EMBODIMENTS

The technical solutions in the embodiments of the present disclosure will be described clearly and completely below in conjunction with the accompanying drawings in the embodiments of the present disclosure; apparently, only some but not all embodiments of the present disclosure are described. All of other embodiments, obtained by those ordinarily skilled in the art based on the embodiments of the present disclosure without using any creative efforts, shall fall into the scope of protection of the present disclosure.

Figure 1:
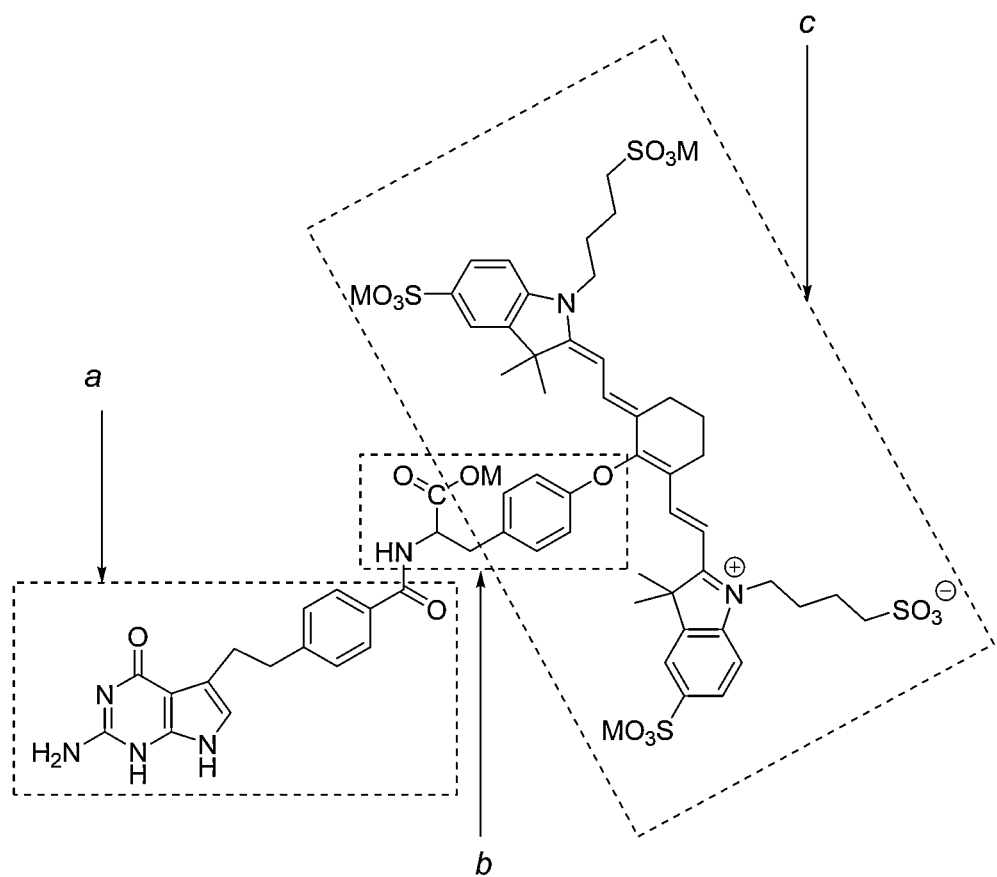
FIG. 1 is a structural diagram of an active targeting near-infrared fluorescent molecule of the present disclosure.

As shown in FIG. 1, the present disclosure takes

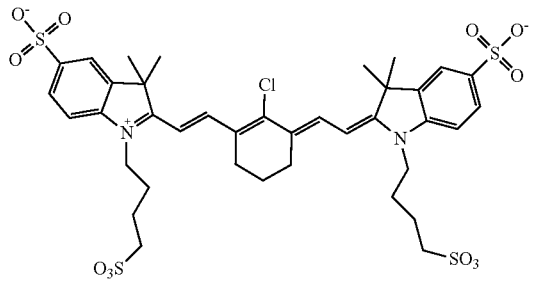

as a matrix, and S0456 and Pemetrexed are structurally linked together through tyrosine to finally form the active targeting near-infrared fluorescent molecule. In FIG. 1, moiety a is Pemetrexed structure, moiety b is tyrosine structure, moiety c is S0456 structure, and M is independently selected from H, Na, and K.

In the present embodiment, a following structural formula is taken as an example:

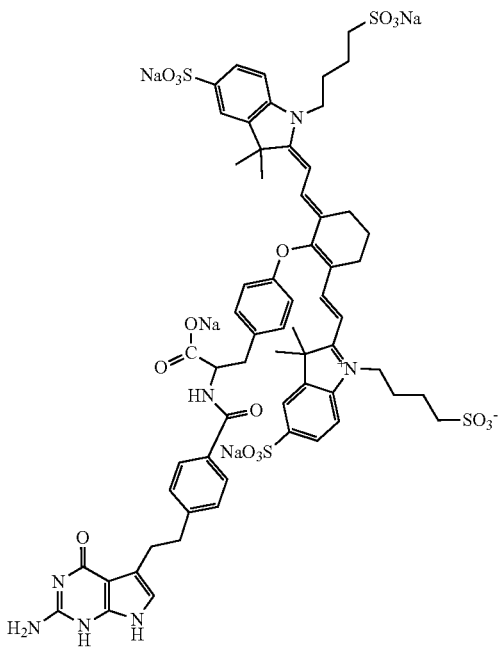

A synthetic process thereof is as follows.

Figure 2:
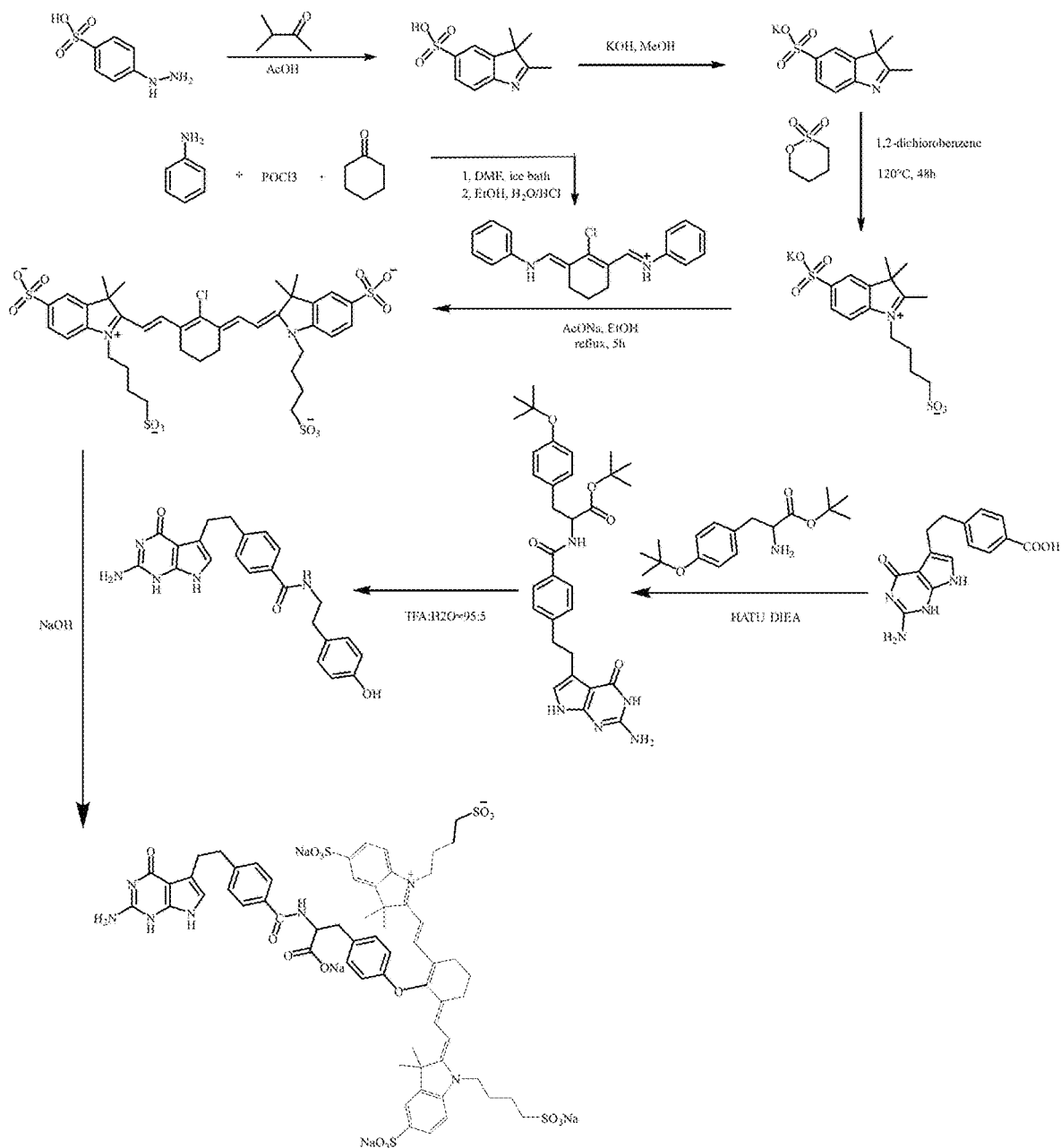
FIG. 2 is a synthetic flow diagram for preparation of the active targeting near-infrared fluorescent molecule.

As shown in FIG. 2, the synthetic process of the active targeting near-infrared fluorescent molecule of the present disclosure includes following steps:

Synthesizing S0456:

(1) 4-hydrazinophenylsulfonic acid (1.6 g, 31.9 mmol), 3-methyl-2-butane (2.10 ml, 90 mmol), and glacial acetic acid (50 ml) were mixed and heated to 120° C. in nitrogen atmosphere for 18 h, After precipitation in ethyl acetate, a crude product was filtered and collected in a form of pink solid, and a resulting product (6.5 g, 25.4 mmol) was dissolved in methanol (50 mL). A dissolving solution was dropwise added into a solution of potassium hydroxide (1.7 g, 30 mmol) and isopropanol (20 ml) under mild conditions, and the crude mixture was filtered and washed to obtain a brown solid, with yield of 97%, and a structural formula of the brown solid is as follows:

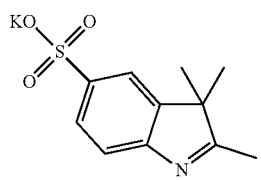
(1)

(2) Product 1 (2.3 g, 8.3 mmol) and 1,4-butyl sultone was added into a toluene solution in nitrogen atmosphere to be heated at 110° C. for 48 h. Mixed materials were cooled to room temperature and a solvent was precipitated. To a crude mixture methanol (10 ml) was added and the resultant was stirred for 30 minutes. Crude mixture was filtered; the resultant was collected, and dissolved in a mixture of water (10 ml) and methanol (50 ml) at 2:1 (v/v). The mixed solution was slowly added to acetonitrile (160 ml) with a dropping funnel. A precipitate was filtered and a pink solid was collected with yield of 40%, wherein a structural formula of the pink solid is as follows:

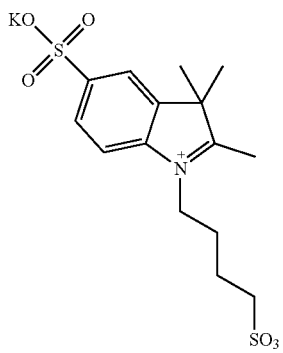
(2)

(3) Product 2 (1.5 g, 2.79 mmol), (chloromethylene)dimethyliminium chloride (Vilsmeier-Haack Reagent™) (0.5 g, 1.39 mmol), and anhydrous sodium acetate (0.342 g, 4.17 mmol) were refluxed and heated in 20 mL of anhydrous ethanol for 6 hours in nitrogen atmosphere. Reaction mixture was cooled to room temperature, and then filtered, washed with ethanol and methanol, and a brownish green solid (S0456) was collected with yield of 90%, wherein a structural formula of the product is as follows:

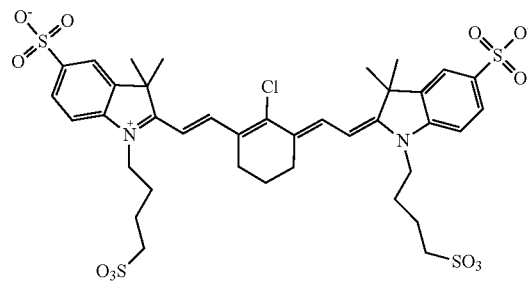
(3)

Figure 5:
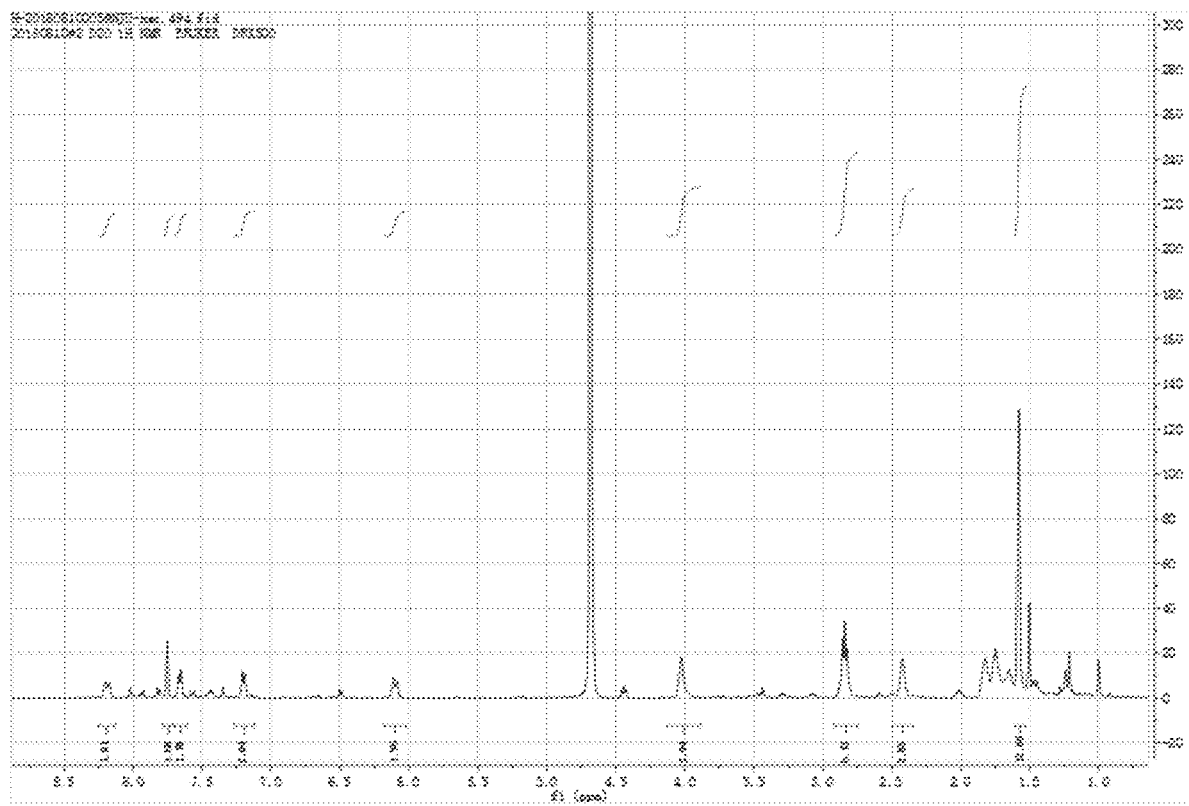
FIG. 5 is a hydrogen spectrum of S0456 of the active targeting near-infrared fluorescent molecule prepared.
Figure 6:
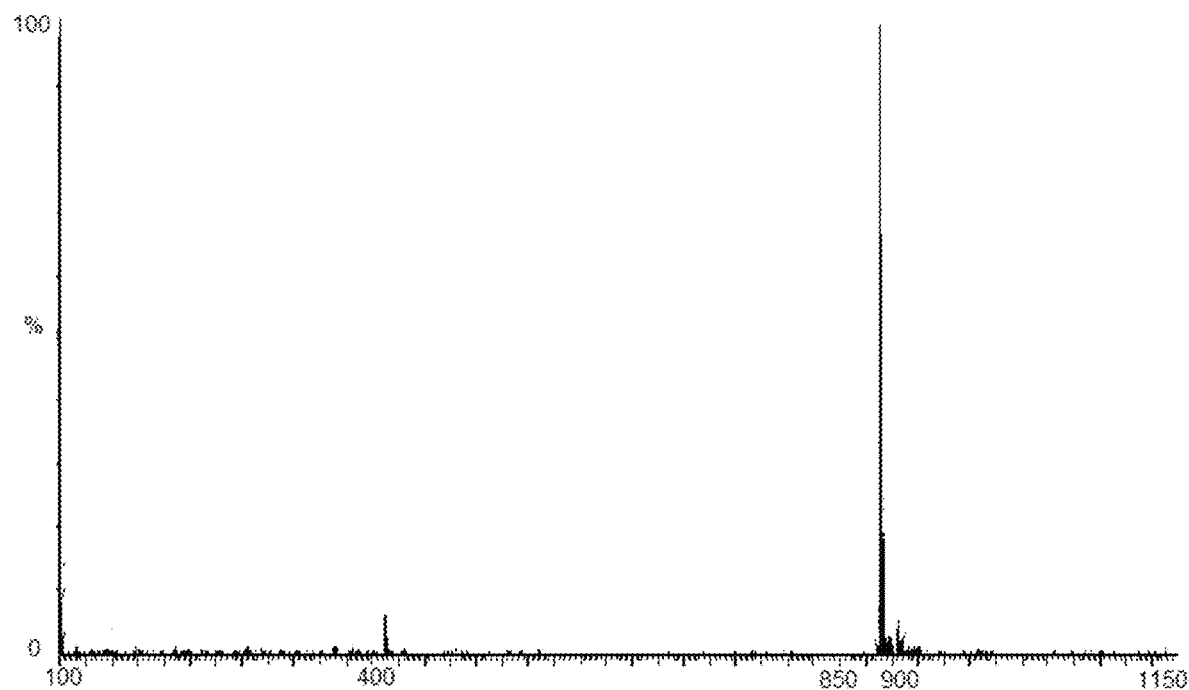
FIG. 6 is a mass spectrum of S0456 of the active targeting near-infrared fluorescent molecule prepared.

FIG. 5 and FIG. 6 show hydrogen spectrum and mass spectrum of S0456, respectively.

Synthesizing a targeted drug: a pemetrexed hydrolytic acid (1.05 g, 3.52 mmol) was dissolved in DMF, and stirred until the resultant was dissolved, Hexafluorophosphate Azabenzotriazole Tetramethyl Uronium (HATU) (2.007 g, 5.28 mmol), O-tert-butyl-L-tyrosine tert-butyl ester hydrochloride (1.161 g, 3.52 mmol), and DIEA (1.364 g, 10.56 mmol) were sequentially added into a flask, and stirred until the resultant was dissolved completely, the reaction was carried out at room temperature for 30 minutes under the protection of nitrogen, and the reacted solution was dropwise added into 0.1 N aq. HCl (1.0 L, 0.14 M) to generate a light yellow precipitate, followed by suction filtration and vacuum drying to obtain (5) 2.04 g of a solid with yield of 95%, wherein a structural formula of the product is as follows:

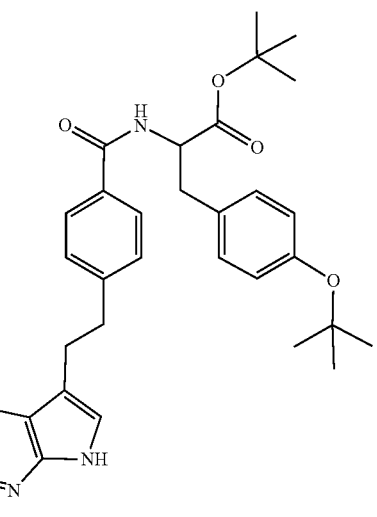
(4)

Figure 7:
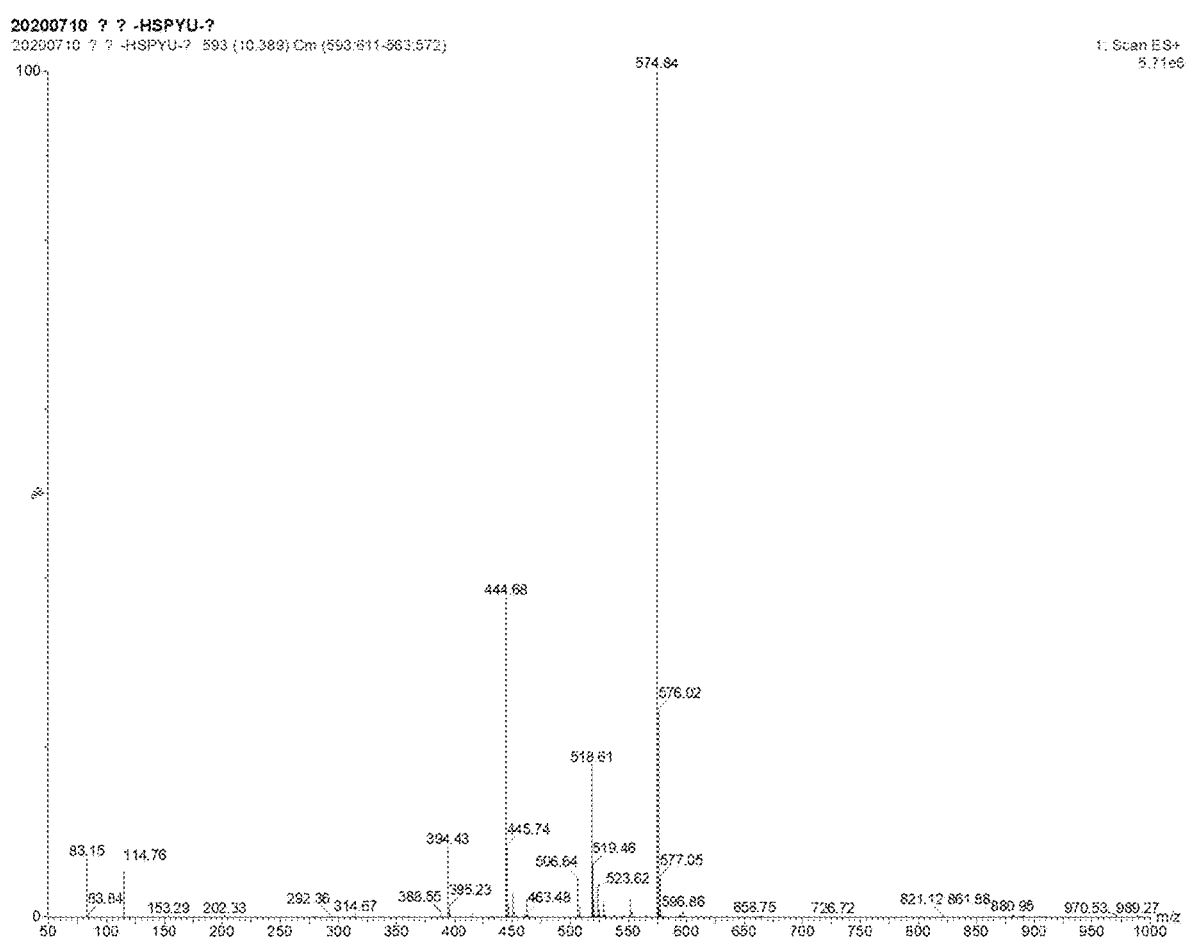
FIG. 7 is a mass spectrum of Pemetrexed-Tyr (OtBu)-OtBu prepared.

The mass spectrum of Pemetrexed-Tyr (OtBu)-OtBu is as shown in FIG. 7.

Solid 4 (2.04 g, 3.34 mmol) was placed in a round-bottom flask, TFA and H$_2$O (95:5, 10 mL) were added, the resultant was stirred for two hours, methyl tert-butyl ether was added, followed by precipitation, filtration, and vacuum drying, to obtained 1.507 g of product with yield of 98%, wherein a structural formula of the product is as follows:

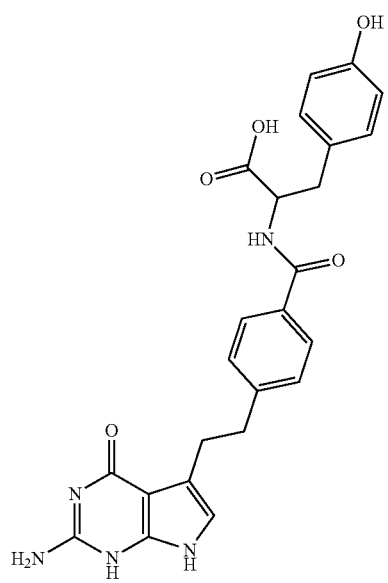
(5)

Figure 8:
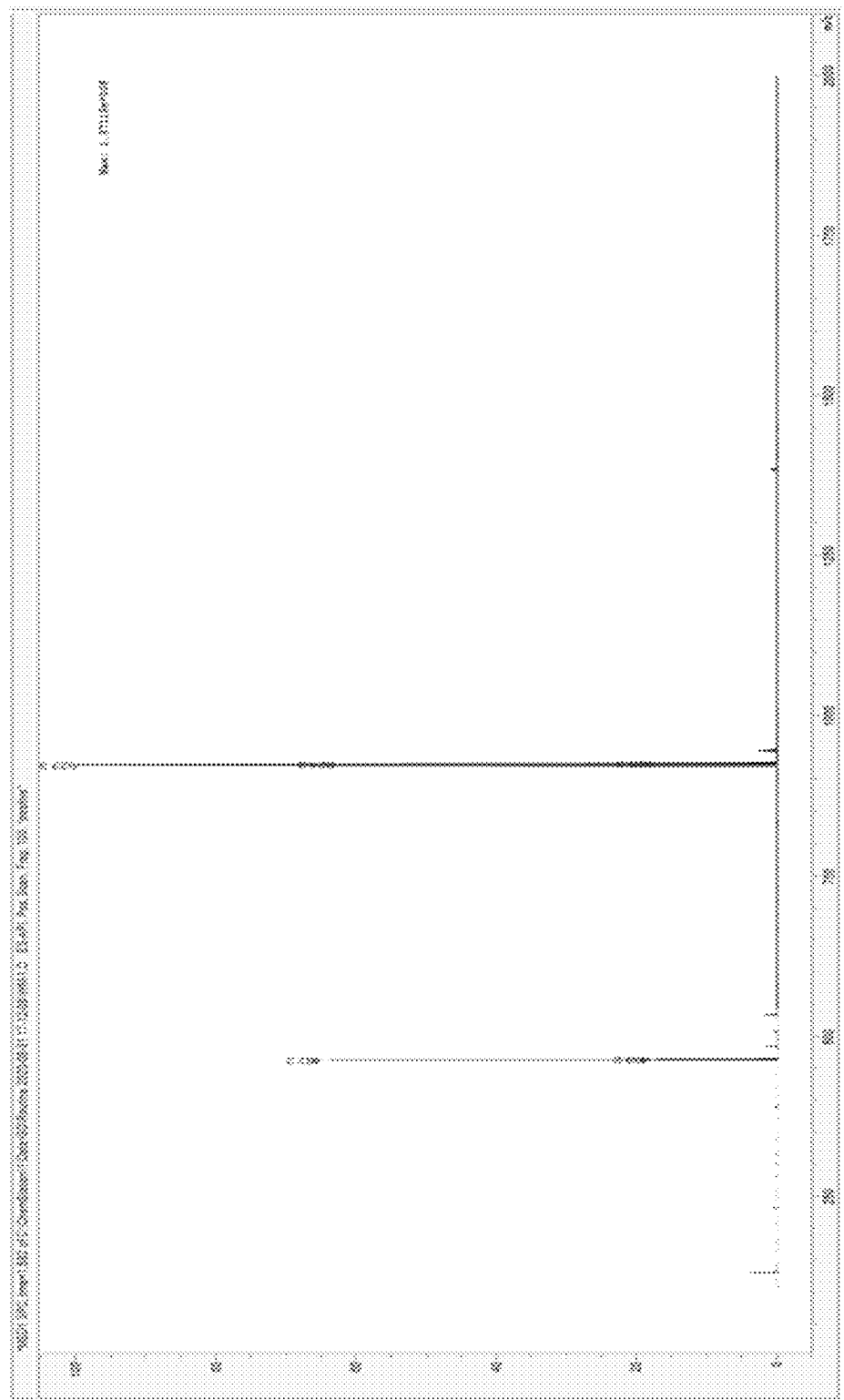
FIG. 8 is a mass spectrum of Pemetrexed-Tyr-OH prepared.

The mass spectrum of Pemetrexed-Tyr-OH is as shown in FIG. 8.

Preparing Pemetrexed-Tyr-S0456: to an aqueous (18 mL) solution of S0456 (2.909 g, 3.276 mmol), a Pemetrexed-Tyr (1.507 g, 3.276 mmol) trianion solution with pH of 11 was added dropwise at 23° C. The temperature of reaction mixture was raised to 90° C., the reaction mixture was stirred at 90° C. for 45 minutes, and formation of 7 was monitored by TLC. After the formation of product was completed, the reaction mixture was cooled to room temperature, and transferred into stirred acetone (0.5 L) as a stable flow through a cannula, to obtain a green precipitate. The precipitate was filtered on a sintering funnel under the vacuum by an air pump, and washed with acetone (3×500 mL). The green powder-like solid was dried in high vacuum for 12 h, and 6 (4.34 g) was quantitatively obtained.

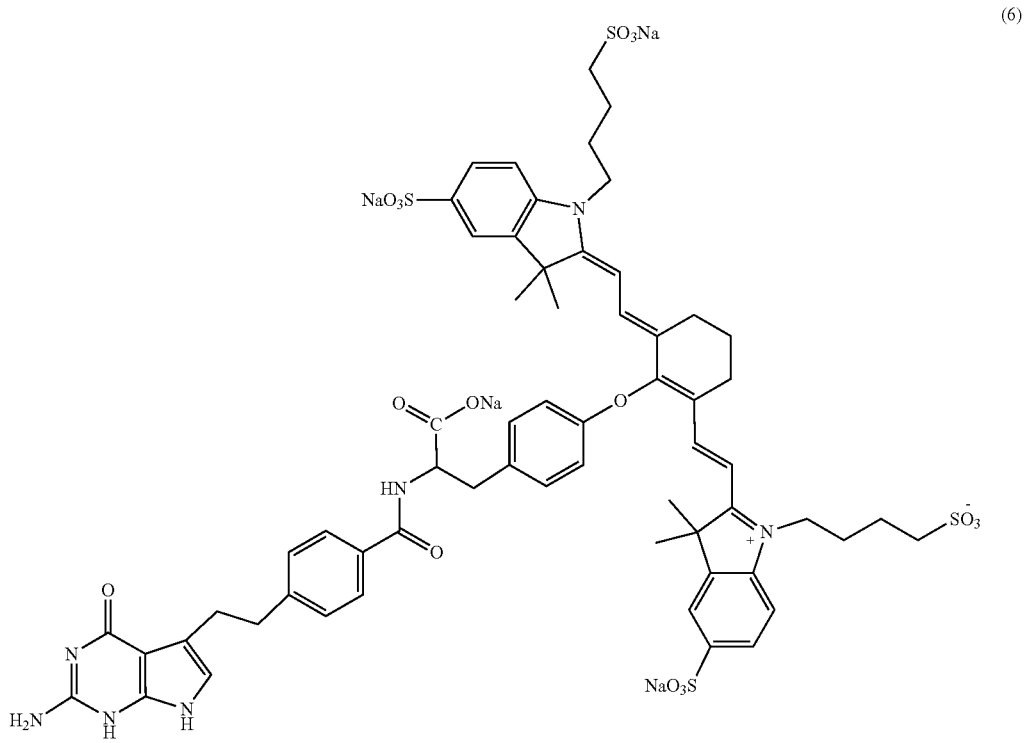

Figure 3:
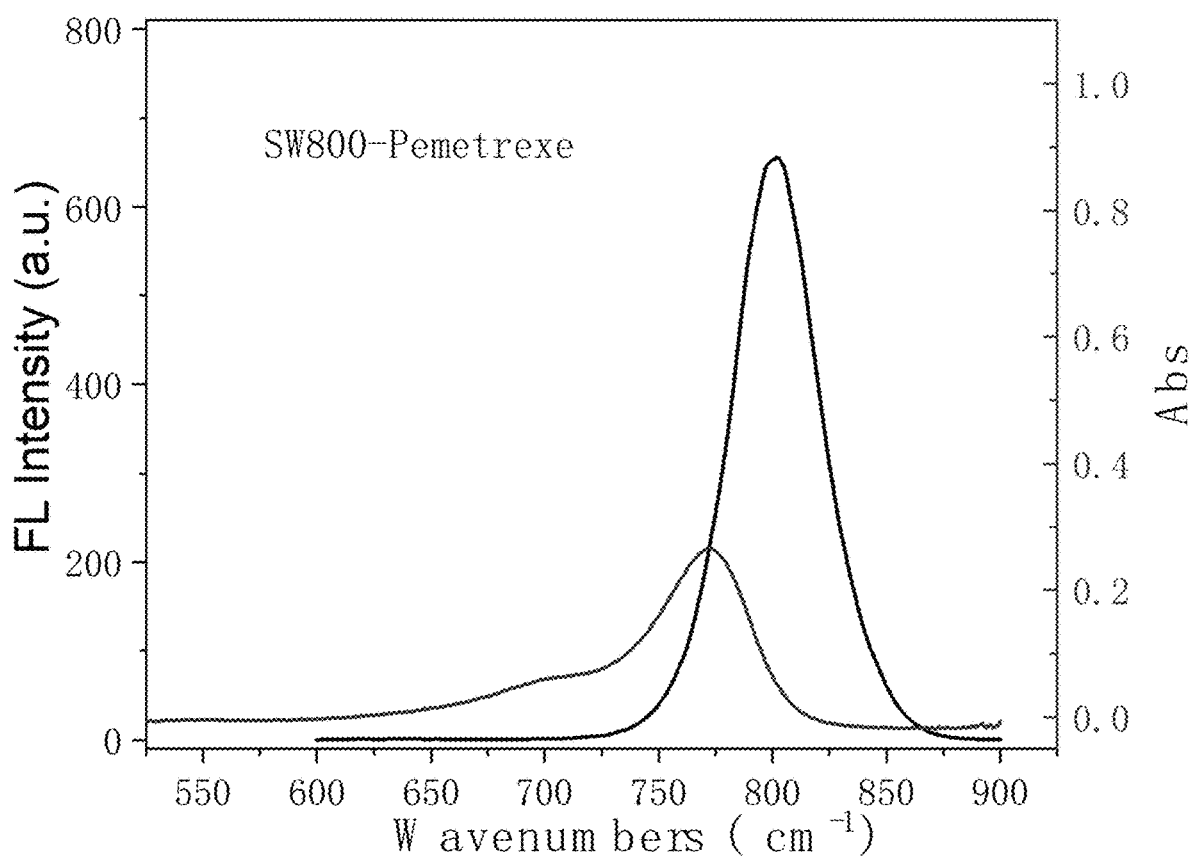
FIG. 3 is a fluorescence performance diagram (fluorescence intensity) of the active targeting near-infrared fluorescent molecule prepared (Excitation (785 nm) and Emission (811 nm))
Figure 4:
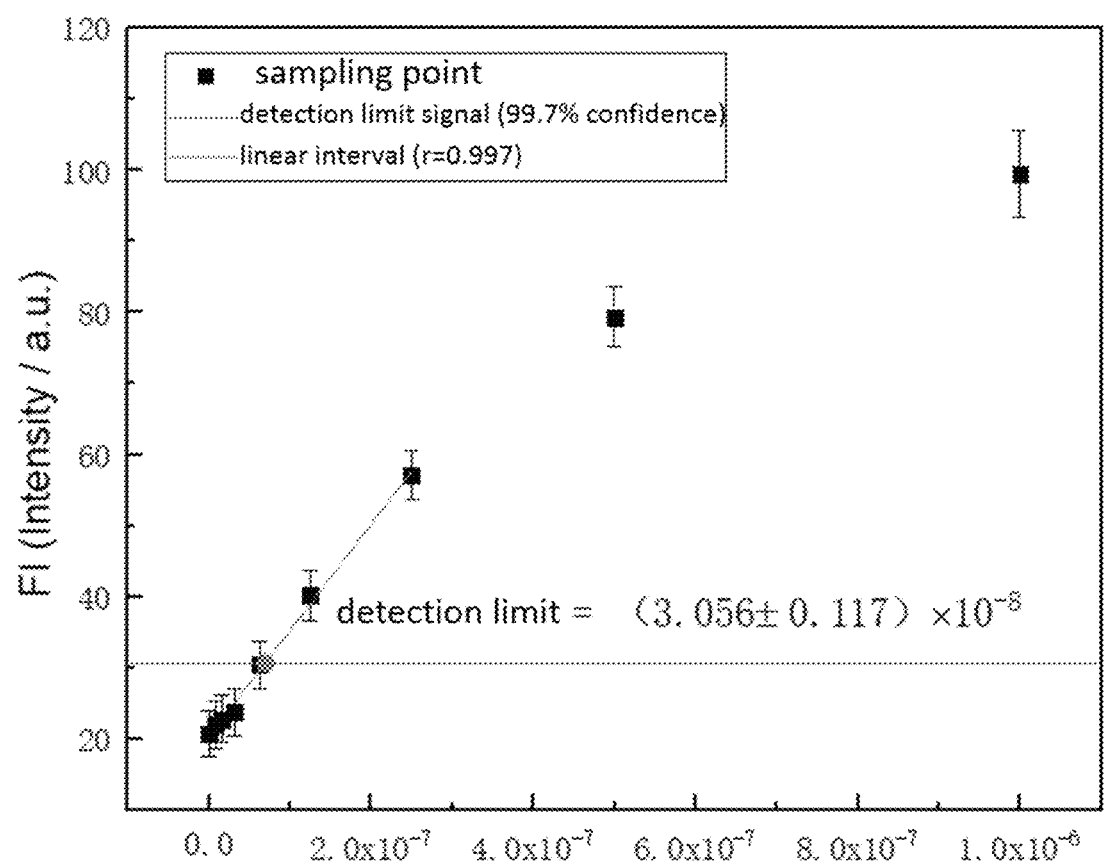
FIG. 4 is a fluorescence performance diagram (detection limit) of the active targeting near-infrared fluorescent molecule prepared (the fluorescence intensity was measured for samples of different concentrations, and this detection limit was determined by linear simulation)
Figure 9:
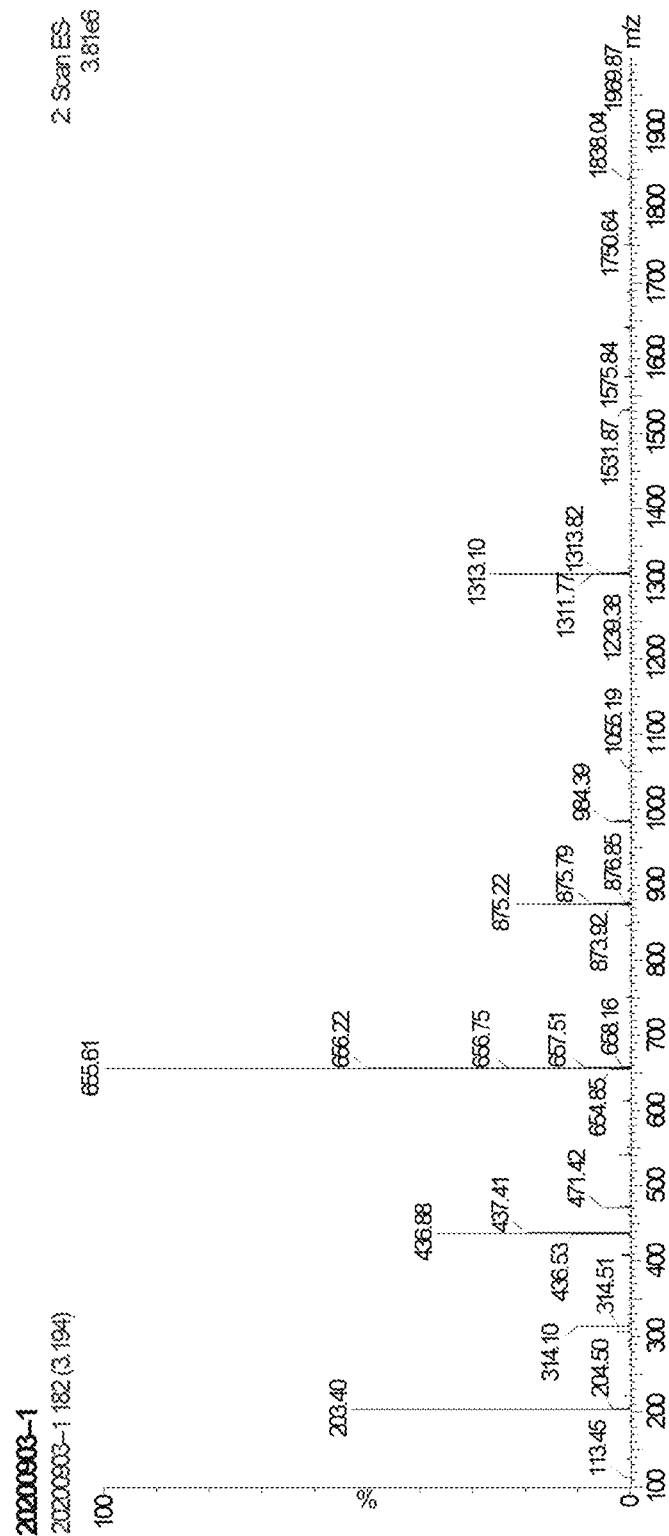
FIG. 9 is a mass spectrum of Pemetrexed-Tyr-50456 prepared.

Upon test, the fluorescence performance spectrum of the Pemetrexed-Tyr-S0456 product is shown in FIG. 3 and FIG. 4, and the mass spectrum is as shown in FIG. 9.

In order to verify effects of the present disclosure, the following verification experiment was performed.

Figure 10:
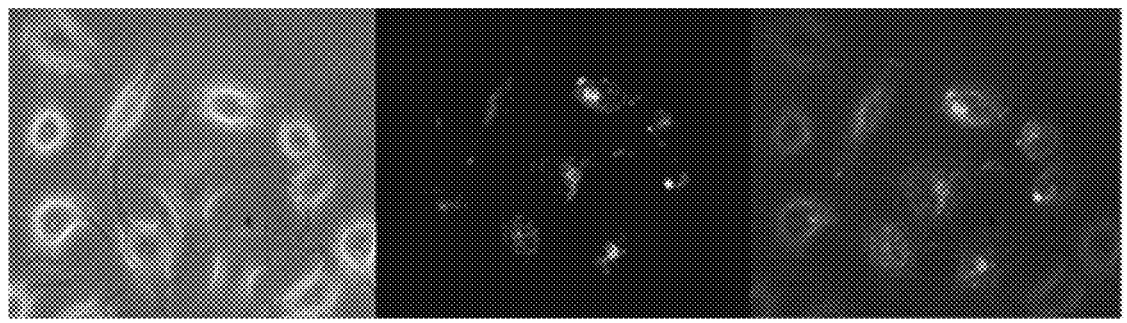
FIG. 10 is a fluorescence microscopic image of the Pemetrexed-Tyr-50456 uptake by KB cells.

KB cells were incubated with 1×10−6 mol/L Pemetrexed-Tyr-S0456 for 2 hours, the cells were washed with PBS for 2-3 times, and then the KB cells were imaged with a laboratory self-made near-infrared fluorescent microscope to obtain white-light and fluorescent images, and images were fused with Image-J, as shown in FIG. 10. Bright KB cells indicate that small molecules target the folate receptor of KB cells, and fluorescence intensity was detected under excitation of excitation light.

The above-mentioned are merely for preferred specific embodiments of the present disclosure; but the scope of protection of the present disclosure is not limited thereto. Equivalent substitutions or changes made by any person familiar with the technical field, according to the technical solution of the present disclosure and improved concept thereof, within the technical scope disclosed in the present disclosure, should be covered within the scope of protection of the present disclosure.

What is claimed is:

1. A near-infrared fluorescent molecule active targeting a folate receptor, with a structural formula as follows:

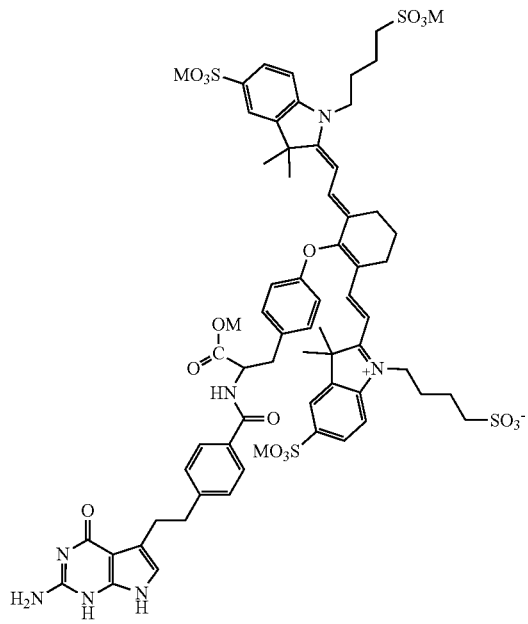

wherein M is independently selected from the group consisting of H, Na, and K.

2. A method for preparing a near-infrared fluorescent molecule active targeting a folate receptor of claim 1, comprising:
- reacting 4-hydrazinophenylsulfonic acid with 3-methyl-2-butane to prepare a product 1;
- reacting the product 1 with 1,4-butyl sultone to prepare a product 2;
- reacting the product 2 with (chloromethylene)dimethyliminium chloride, aminobenzene, and cyclohexanone to prepare a product 3;
- reacting pemetrexed hydrolytic acid with Hexafluorophosphate Azabenzotriazole Tetramethyl Uronium (HATU) and O-tert-butyl-L-tyrosine tert-butyl ester hydrochloride to prepare a product 4;
- reacting the product 4 with trifluoroacetic acid to prepare a product 5; and
- reacting the product 3 and the product 5 to prepare the near-infrared fluorescent molecule active targeting a folate receptor of claim 1, wherein a structural formula of the product 1 is as follows:

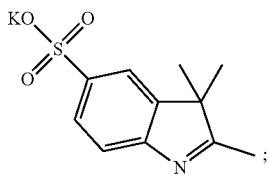

a structural formula of the product 2 is as follows:

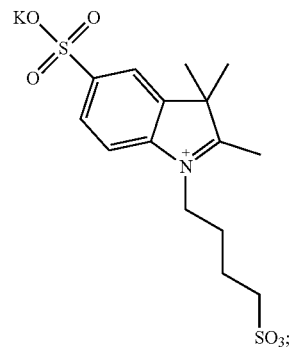

a structural formula of the product 3 is as follows:

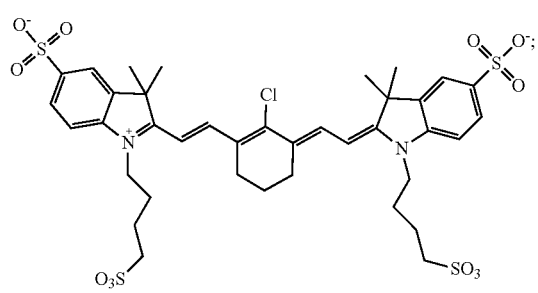

a structural formula of the product 4 is as follows:

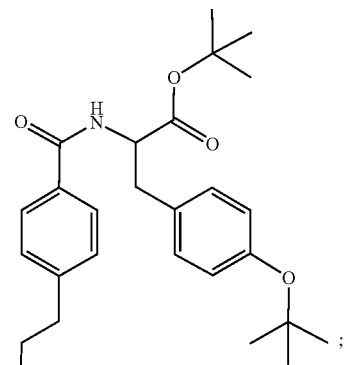

and
a structural formula of the product 5 is as follows:

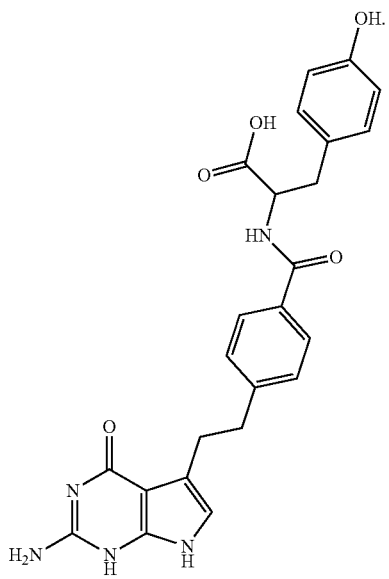 [SMILES: Nc1nc(=O)c2c(CCc3ccc(C(=O)NC(Cc4ccc(O)cc4)C(=O)O)cc3)c[nH]c2[nH]1]

3. The method of claim 2,
wherein,
the product 1 is obtained by reacting 4-hydrazinophenylsulfonic acid and the 3-methyl-2-butane in glacial acetic acid at 110-130° C.;

the product 2 is obtained by reacting the product 1 with 1,4-butyl sultone at 100-120° C.;

the product 3 is obtained by reacting the product 2, (chloromethylene)dimethyliminium chloride, aminobenzene, cyclohexanone and anhydrous sodium acetate in anhydrous ethanol;

the product 4 is obtained by dissolving pemetrexed hydrolytic acid in DMF, and by sequentially adding Hexafluorophosphate Azabenzotriazole Tetramethyl Uronium (HATU), 0-tert-butyl-L-tyrosine tert-butyl ester hydrochloride, and N,N-diisopropylethylamine (DIEA); and the near-infrared fluorescent molecule active targeting a folate receptor of claim 1 is obtained by adding a solution of the product 5 to an aqueous solution of the product 3 at pH 10-12 at 18-28° C.

* * * * *

UNITED STATES PATENT AND TRADEMARK OFFICE
CERTIFICATE OF CORRECTION

PATENT NO. : 11,718,625 B2  
APPLICATION NO. : 17/596423  
DATED : August 8, 2023  
INVENTOR(S) : Huiming Cai et al.

Page 1 of 1

It is certified that error appears in the above-identified patent and that said Letters Patent is hereby corrected as shown below:

On the Title Page

"(73) Assignee: NANJING UOYUAN MEDICAL DEVICES CO., LTD, Jiangsu (CN)" should read,
-- (73) Assignee: NANJING NUOYUAN MEDICAL DEVICES CO., LTD, Jiangsu (CN) --

Signed and Sealed this  
Fifth Day of December, 2023

Katherine Kelly Vidal  
*Director of the United States Patent and Trademark Office*